United States Patent
Zeidan et al.

(10) Patent No.: US 10,905,349 B1
(45) Date of Patent: Feb. 2, 2021

(54) MAPPING ATRIAL FIBRILLATION USING FRAGMENTATION INDEX

(71) Applicant: Biosense Webster (Israel) Ltd., Yokneam (IL)

(72) Inventors: Ziyad Zeidan, Zemmer (IL); Aharon Turgeman, Zichron Ya'acov (IL); Benjamin Cohen, Haifa (IL); Yaron Kadoshi, Hosha'aya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 47 days.

(21) Appl. No.: 16/512,588

(22) Filed: Jul. 16, 2019

(51) Int. Cl.
    *A61B 5/046* (2006.01)
    *A61B 5/044* (2006.01)

(52) U.S. Cl.
    CPC .............. *A61B 5/046* (2013.01); *A61B 5/044* (2013.01)

(58) Field of Classification Search
None
See application file for complete search history.

(56) References Cited

U.S. PATENT DOCUMENTS

| | | | |
|---|---|---|---|
| 2007/0250129 A1* | 10/2007 | Van Oort | A61B 5/0452 607/28 |
| 2015/0359430 A1 | 12/2015 | Bem-Haim | |
| 2017/0367601 A1 | 12/2017 | Bars et al. | |

FOREIGN PATENT DOCUMENTS

| | | |
|---|---|---|
| EP | 2064990 A1 | 6/2009 |
| EP | 2851002 A1 | 3/2015 |
| WO | WO2010054409 A1 | 5/2010 |

OTHER PUBLICATIONS

European Search Report for corresponding EPA No. 20185867.7 dated Nov. 30, 2020.

* cited by examiner

*Primary Examiner* — Brian T Gedeon (57) ABSTRACT

A method for mapping atrial fibrillation (AF) in a heart, the method includes receiving an electrogram (EGM) signal, which is acquired at a given position in the heart, and is exhibiting the AF. Two or more primary peaks are identified in the EGM signal, and a cycle length (CL) is calculated between adjacent primary peaks. One or more secondary peaks are identified in the EGM signal within the CL. A local fragmentation index (FI) that is indicative of a number of the secondary peaks per CL, is calculated. The local FI is visualized on a map of at least part of the heart.

12 Claims, 4 Drawing Sheets

MAPPING ATRIAL FIBRILLATION USING FRAGMENTATION INDEX

FIELD OF THE INVENTION

The present invention relates generally to electrophysiological mapping, and particularly to methods and systems for mapping atrial fibrillation using a fragmentation index.

BACKGROUND OF THE INVENTION

Atrial fibrillation is an irregular heart rhythm generated in the atria. Various techniques for mapping atrial fibrillation are known in the art.

For example, U.S. Patent Application Publication 2017/0367601 describes a method for identifying areas of the heart of a patient able to be involved in the perpetuation of atrial fibrillation. This method takes into account the reference cycle of the arrhythmia and has two variants: a local variant in which the areas of the heart are each analyzed separately and a regional variant in which several areas of the heart are analyzed together.

U.S. Patent Application Publication 2015/0359430 describes a method of medical image processing for images of body structures, the method comprising: receiving anatomical data to reconstruct an anatomical image of a region of a body of a patient, said region comprises a portion of at least one internal body part which borders or is spaced apart from a target tissue; receiving functional data from a functional imaging modality which images at least said portion of the region of the body of the patient; processing said anatomical image to generate at least one image mask corresponding to the zone outside of the wall of said at least one internal body part; correlating the at least one generated image mask with the functional data for guiding a reconstruction of a functional image depicting said target tissue; and providing the reconstructed functional image.

U.S. Patent Application Publication 2012/0078129 describes a method of displaying an image of the location of one or more low voltage structures in tissue. The method includes receiving electrical mapping data corresponding to a portion of the tissue, and generating an image using the electrical mapping data. Electrical mapping values within at least one voltage range having two endpoints that bound the upper and lower limits of the voltage range are distinguishable from electrical mapping values outside the at least one voltage range. The two endpoints are selected to distinguish the one or more low voltage structures of the tissue from other portions of the tissue.

SUMMARY OF THE INVENTION

An embodiment of the present invention that is described herein provides a method for mapping atrial fibrillation (AF) in a heart, the method including receiving an electrogram (EGM) signal, which is acquired at a given position in the heart, and is exhibiting the AF. Two or more primary peaks are identified in the EGM signal, and a cycle length (CL) is calculated between adjacent primary peaks. One or more secondary peaks are identified in the EGM signal within the CL. A local fragmentation index (FI) that is indicative of a number of the secondary peaks per CL, is calculated. The local FI is visualized on a map of at least part of the heart.

In some embodiments, the heart has a region that includes (i) the given position located at a given distance from a predefined location of the region, and (ii) at least an additional position having an additional FI and located at an additional distance from the predefined location, and the method includes calculating and visualizing, based on the given distance and the additional distance, and based on the local FI and the additional FI, a regional FI of the region. In other embodiments, the predefined location includes a geometrical center of gravity (COG) of the region, and calculating and visualizing the regional FI includes calculating, based on the given distance and the additional distance, a weighted average of at least the local FI and the additional FI. In yet other embodiments, identifying the one or more secondary peaks includes merging, based on a predefined threshold, two or more adjacent secondary peaks.

In an embodiment, the method includes defining a window of interest (WOI) within the CL, and identifying the one or more secondary peaks within the WOI. In another embodiment, the EGM signal includes multiple CLs, and calculating the local FI includes calculating, based on the multiple CLs, an average CL, and calculating an average number of the secondary peaks per the average CL.

There is additionally provided, in accordance with an embodiment of the present invention, a system for mapping atrial fibrillation (AF) in a heart, the system includes a processor and a display. The processor is configured to: (a) receive an electrogram (EGM) signal exhibiting the AF, which is acquired at a given position in the heart, (b) identify, in the EGM signal, two or more primary peaks and calculate a cycle length (CL) between adjacent primary peaks, (c) identify, in the EGM signals, one or more secondary peaks within a duration of the CL, and (d) calculate a local fragmentation index (FI) that is indicative of a number of the secondary peaks per CL. The display is configured to display the local FI on a map of at least part of the heart.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Some medical procedures are based on measuring electrogram (EGM) signals by disposing a plurality of electrodes at different respective sites on the cardiac tissue. In some cardiac procedures, a physician may use the EGM signals to characterize the propagation of the wavefront of electrical activation through the cardiac tissue of a patient during a cardiac cycle. For each of the EGM signals, the physician may attempt to identify electrical activation points that correspond to an instance at which the wavefront passed through the site at which the signal was acquired.

In cases of heart atrial fibrillation (AF) or other arrhythmias, it may be difficult, even for an experienced physician, to identify such activation points, due to irregularity and/or variability of the EGM signals. Regular electrograms typically contain regularly-spaced and sharp primary peaks that clearly indicate electrical activations. In contrast, irregular EGMs may exhibit a wide variety of different forms, and may comprise numerous bursts of secondary peaks that are typically not indicative of regular electrical activation.

Embodiments of the present invention that are described hereinbelow provide methods and systems for mapping AF by calculating local and regional fragmentation indexes (FIs), and visualizing the FIs on a map of a patient heart. In some embodiments, a system for mapping AF in a patient heart comprises a processor and a display.

In some embodiments, the processor is configured to receive, from a catheter inserted into a patient heart, an EGM signal that exhibits the AF and acquired at a given position in the heart. The processor is further configured to identify, in the EGM signal, two or more primary activation peaks, also referred to herein as annotations, and to calculate a cycle length (CL) between adjacent annotations. The processor is further configured to hold predefined criteria for identifying a regular atrial fibrillation cycle length (AFCL), such as but not limited to, a cycle length between 120 ms (referred to herein as short AFCLs) and 250 ms (referred to herein as long AFCLs) having a standard deviation smaller than 30 ms.

In some embodiments, the processor is configured to define a window of interest (WOI) within the AFCL, and to identify within the WOI, one or more secondary activation peaks, also referred to herein as fragmentation peaks. The processor calculates at the given position, a local fragmentation index (FI) that is indicative of an average number of the fragmentation peaks per WOI.

In some embodiments, the processor is configured to merge, based on a predefined threshold and criteria, two or more adjacent fragmentation peaks. In some embodiments, the EGM signal comprises multiple AFCLs, and the processor is configured to calculate, based on the multiple AFCLs, an average AFCL, and to calculate an average number of the fragmentation peaks per the average AFCL. In some embodiments, the display is configured to display the calculated and visualized local FI on a map of at least part of the heart.

In some embodiments, a region of patient heart contains the given position, which is located at a given distance from a geometrical center-of-gravity (COG) of the region. The region additionally comprises multiple positions located at respective distances from the COG. In such embodiments, the processor is configured to acquire, using the catheter, additional EGM signals at the additional respective positions, and to calculate, for each of the additional positions, a respective additional FI.

In some embodiments, the processor is configured to calculate, based on the given distance and the additional distances, and based on the local FI and the additional FIs, a regional FI of the region. The processor is further configured to output, to the display, a visualization of the regional FI and the AFCLs. The display is configured to display the calculated and visualized regional FI on a map of the heart showing at least the aforementioned region, and to display the short and the long AFCLs, overlaid on the regional FIs. In such embodiments, the processor is configured to display, on the heart map, important regions, such as regions having short AFCLs and large regional FI.

The disclosed techniques provide the physician with the features of detection and display of regions suspected to have irregular activation. The physician may apply ablation in one or more of the suspected regions, in order to reduce the arrhythmia in the patient heart.

System Description

Figure 1:
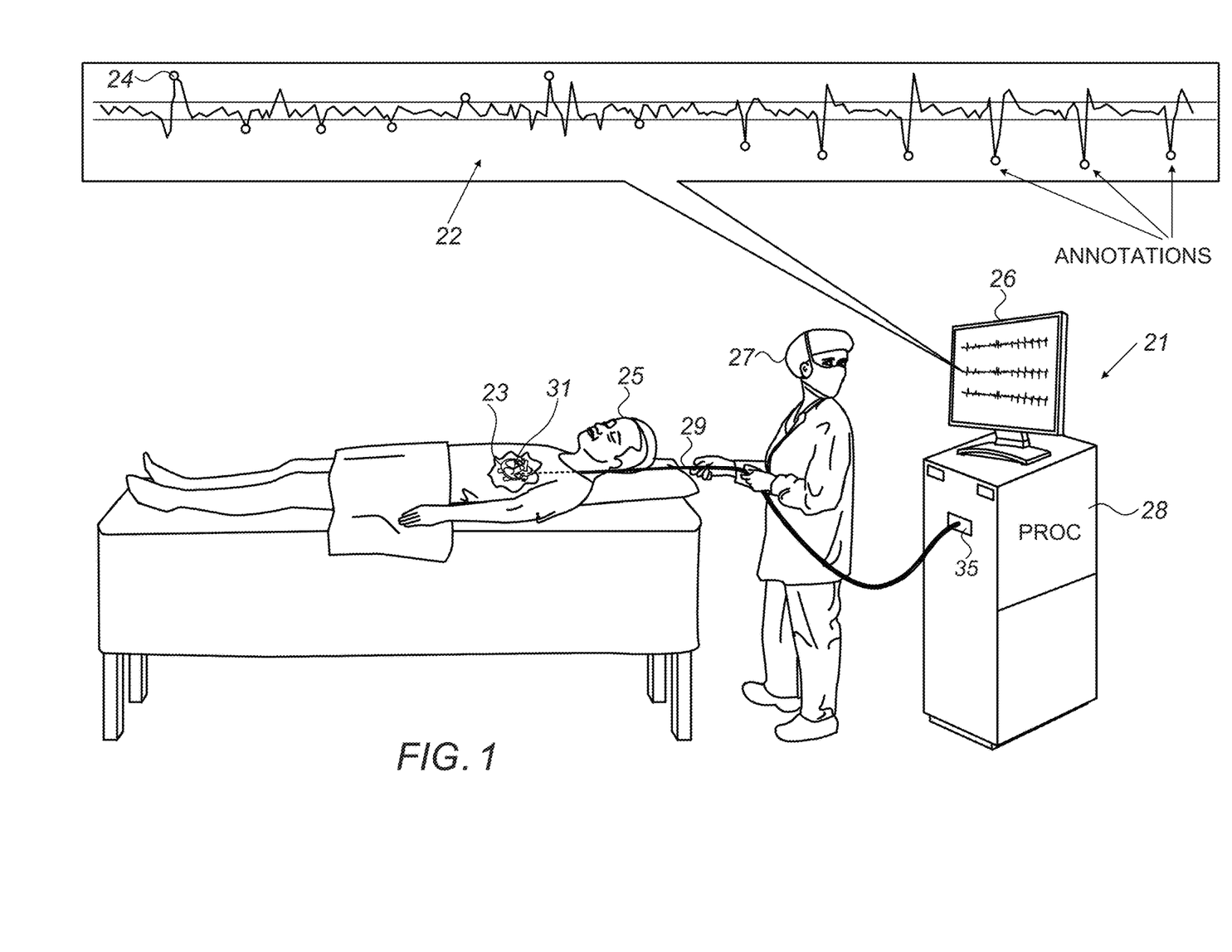
FIG. 1 is a schematic, pictorial illustration of a system for annotating an electrogram (EGM) signal, in accordance with an embodiment of the present invention.

FIG. 1 is a schematic, pictorial illustration of a system 21 for annotating an electrogram (EGM) signal 22, in accordance with an embodiment of the present invention. As shown in FIG. 1, during an electrophysiological (EP) procedure, a physician 27 inserts a catheter 29 and navigates a distal end 31 of catheter 29 into a desired location in a heart 23 of a patient 25.

In some embodiments, when physician 27 moves distal end 31 of catheter 29 along the inner epicardial surface, also referred to herein as tissue, of heart 23, one or more electrodes (not shown) disposed at distal end 31 of catheter 29, which are in contact with tissue of the heart, sense EGM signals 22 generated by the tissue. Such signals may be sensed, for example, while heart 23 experiences atrial fibrillation (AF) or any other arrhythmia. Note that in some cases, the arrhythmia may be induced by the physician as part of the procedure.

In some embodiments, a processor 28 of system 21 receives EGM signals 22 from distal end 31, via an electrical interface 35, such as a socket or port, and processes these EGM signals as will be described in detail in FIGS. 2 and 3 below. In some embodiments, in response to processing the EGM signals, processor 28 is configured to generate an output, which typically comprises a visual output displayed on a display 26 of system 21.

In some embodiments, processor 28 is configured to annotate at least one peak of EGM signal 22 to show the activation points of the EGM signal, and to display the annotated signal on display 26. In annotating the signal, processor 28 may, for example, place a marker 24 over each activation point. In the context of the present invention and in the claims, the annotated signal shown by marker 24 is also referred to herein as a "primary peak" or as an "annotated activation signal."

In some embodiments, the electrodes at distal end 31 may be arranged in any suitable configuration, such as a circular, linear, or multi-spline configuration. Typically, each EGM signal 22 may be a bipolar signal, so that the signal represents the voltage between a respective pair of the electrodes at distal end 31. In alternative embodiments, at least one of the acquired EGM signals may be a unipolar signal, so that the EGM signal represents the voltage between one of the electrodes and a reference electrode that is coupled externally to patient 25.

In some embodiments, processor 28 may comprise a single processor, or a cooperatively networked or clustered set of processors. In some embodiments, the functionality of processor 28, as described herein, may be implemented solely in hardware, e.g., using one or more Application-Specific Integrated Circuits (ASICs) or Field-Programmable Gate Arrays (FPGAs). In other embodiments, the functionality of processor 28 may be implemented at least partly in software. For example, in some embodiments, processor 28 may comprise a programmed digital computing device comprising at least a central processing unit (CPU) and random access memory (RAM). In some embodiments, system 21 may comprise any suitable types of non-volatile memory devices.

In other embodiments, processor 28 may comprise a general-purpose processor, which is programmed in software to carry out the functions described herein. The software may be downloaded to the processor in electronic form, over a network, for example, or it may, alternatively or additionally, be provided and/or stored on non-transitory tangible media, such as magnetic, optical, or electronic memory.

This particular configuration of system 21 is shown by way of example, in order to illustrate certain problems that are addressed by embodiments of the present invention and to demonstrate the application of these embodiments in enhancing the performance of such a system. Embodiments of the present invention, however, are by no means limited to this specific sort of example system, and the principles described herein may similarly be applied to other sorts of systems for mapping arrhythmia and to other sorts of systems for annotating and analyzing any suitable signals acquired from any human organ.

Figure 2:
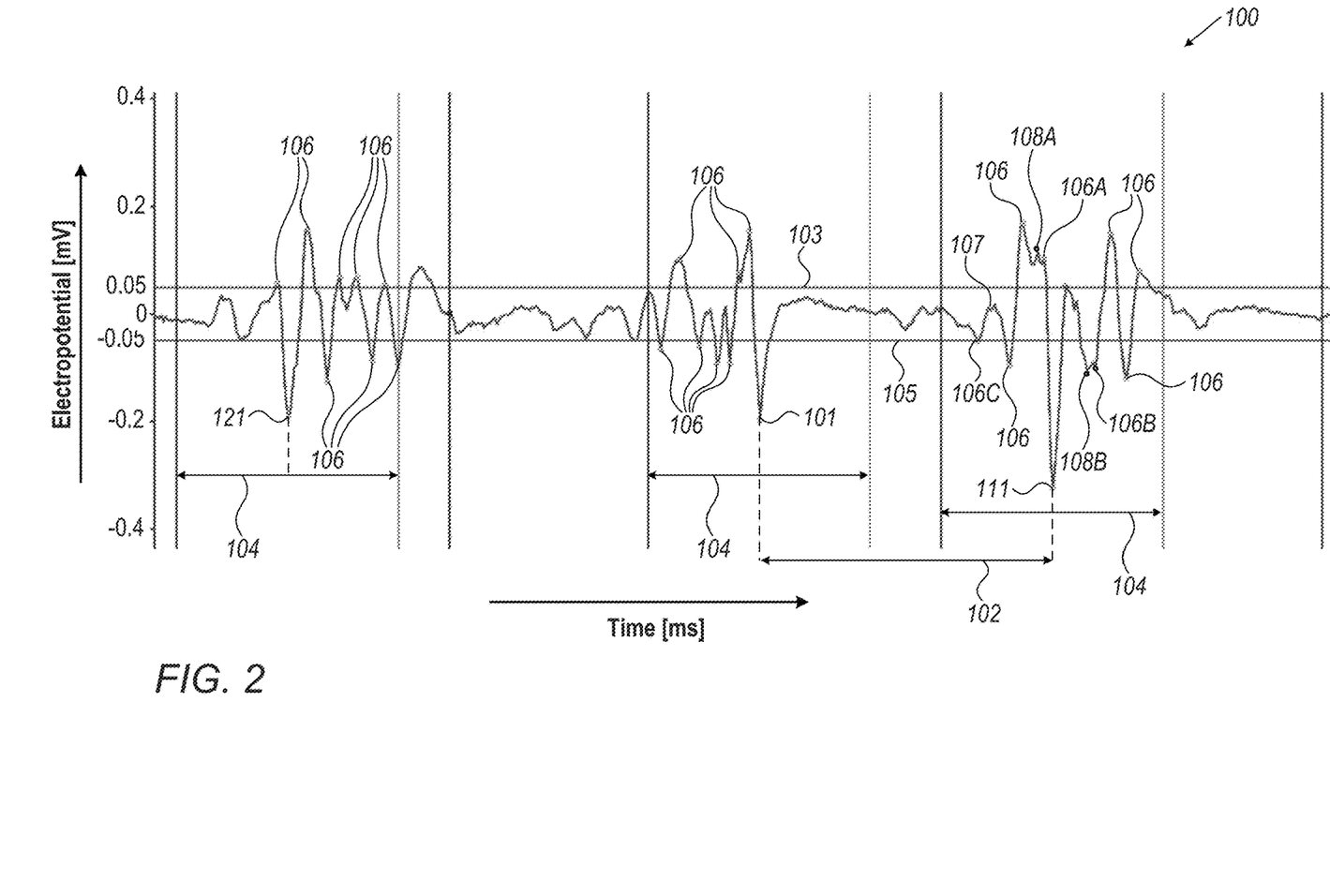
FIG. 2 is a graph showing an identification of activation points in an electrogram signal, in accordance with an embodiment of the present invention.

Calculating Local Fragmentation Index and Cycle Length Based on Identified Primary and Secondary Peaks FIG. 2 is a graph showing an identification of activation points in an EGM signal 100, in accordance with an embodiment of the present invention. EGM signal 100 may replace, for example, EGM signal 22 of FIG. 1 above.

In some embodiments, EGM signal 100 is acquired at a given position in heart 23 using one or more electrodes of distal end 31, and comprises a complex fractionated EGM signal measured in millivolts (mV) over time. In some embodiments, processor 28 is configured to divide the total period that is spanned by the signal into successive smaller time periods, each being of a predefined length or within a range of lengths, e.g., between 100 milliseconds (ms) and 200 ms, or any other suitable period of time.

In some embodiments, processor 28 is configured to select a set of candidate activation points that comprises, for each of the time periods, the point (or "peak") of greatest magnitude within the time period, provided that the greatest magnitude is greater than the threshold for the time period and is also greater than a predefined noise threshold (e.g., 0.05 mV), indicated in FIG. 2 by upper and lower noise-threshold lines 103 and 105. Note that line 103 is located 0.05 mV above the center line of EGM signal 100, and line 105 is located 0.05 mV below the center line of EGM signal 100. Subsequently, processor 28 is configured to remove, from the set of candidate activation points, one of any pair of the candidate points that are within a predefined time interval (e.g., 80 ms) from one another. The points remaining in the set are then assumed to be the annotated activation signals, in the present example, primary peaks 101, 111 and 121.

In some embodiments, processor 28 is configured to calculate an atrial fibrillation cycle length (AFCL) between adjacent annotated activation signals, in the example of FIG. 2, an AFCL 102 between primary peaks 101 and 111. In some embodiments, processor 28 may hold two thresholds used for defining a range of AFCLs that are considered regular for AF. For example, EGM signal 100 may be acquired over a total period of 2500 ms and having seventeen (17) candidate primary peaks and therefore sixteen (16) calculated AFCLs. Each adjacent primary peaks may delimit an AFCL between 120 ms (referred to herein as a short AFCL) and 250 ms (referred to herein as a long AFCL) and having a standard deviation (SD) smaller than 30 ms relative to the calculated 16 AFCLs of EGM signal 100.

In some embodiments, processor 28 is configured to calculate, based on the calculated AFCLs, an average AFCL and to hold two thresholds for the average AFCL and a threshold for the SD. In accordance with the above example, processor 28 may hold thresholds of 120 ms and 250 ms for the lower and higher values of the average AFCL, respectively, and to hold an additional threshold of 30 ms for the AFCL SD.

In some embodiments, processor 28 is configured to define a window of interest (WOI) 104 having a width smaller than the AFCL and/or within the duration of width 102. In the example of FIG. 2, the centers of WOIs 104 are aligned with the respective time of primary peaks 101, 111 and 121 and extend along the time axis +/−40% of the AFCL length. In other words, WOI 104 has an 80% length of the total length of AFCL 102. In other embodiments, processor 28 may hold any other suitable threshold, other than 80%, for defining the length (or time interval) of WOI 104 relative to AFCL 102.

In some embodiments, processor 28 is configured to identify, within WOI 104, a set of candidate fragmentation peaks, also referred to herein as secondary peaks.

Processor 28 is further configured to filter out some of the candidate peaks, using a predefined threshold and criteria, and to obtain a final set of fragmentation peaks.

In the example of FIG. 2, processor 28 identifies candidate peaks 106, 106A, 106B, 106C, 107, 108A and 108B. In an embodiment, processor 28 filters out candidate peak 107, which is below the 0.05 mV noise threshold (i.e., between lines 103 and 105. Note that processor 28 does not filter out peak 106C, which has an absolute value slightly larger than the noise threshold. In an embodiment, processor 28 checks whether all peaks larger than 0.05 mV, i.e., located above line 103, are trending-up over time before the peak and are trending-down over time after the peak. Similarly, processor 28 checks whether all peaks smaller than −0.05 mV, i.e., located below line 105, are trending-down over time before the peak and are trending-up over time after the peak.

In some embodiments, processor 28 is configured to remove, from the set of candidate peaks, at least one of any group of the candidate peaks that are within a predefined time interval (e.g., 20 ms) from one another and having the same sign (positive or negative), and to consolidate the removed one or more peak into the largest peak from among the group. In the example of FIG. 2, peaks 106A and 108A are within the predefined time interval of 20 ms and peak 108A is larger than peak 106A. Therefore, processor 28 removes peak 106A, or in other words, merges peak 106A into peak 108A. Similarly, peaks 106B and 108B are within the predefined time interval of 20 ms and peak 108B has an absolute electro-potential value larger than that of peak 106B. Therefore, processor 28 merges peak 106B into peak 108B. Subsequently, processor 28 produces a final list of the secondary peaks, in the example of FIG. 2 the final list comprises peaks 106, 106C, 108A and 108B selected based on the threshold and criteria described above. Note that the time intervals of 80 ms and 20 ms predefined, respectively, for the primary and secondary peaks, the predefined time interval between 120 ms and 250 ms for the AFCLs, and the predefined noise threshold of +/−0.05 mV, are all provided by way of example. In other embodiments, processor 28 may hold any other suitable one or more thresholds value for any of the above time intervals and/or noise threshold.

In some embodiments, processor 28 is configured to calculate for EGM signal 100 that was acquired at the given location of heart 23, a local fragmentation index (FI) that is indicative of an average number of the secondary peaks per AFCL.

In some embodiments, processor 28 is configured to calculate the local FI using equation (1) given by:

$$\text{Local } FI = \frac{SP}{PP} \times \frac{AWOI}{NWOI} \quad (1)$$

where:

SP is an accumulated number of secondary peaks counted within the actual WOI.

PP is an accumulated number of primary peaks counted within the actual WOI.

AWOI is an accumulated actual time durations of all actual WOIs within EGM signal 100.

NWOI is an accumulated nominal time durations of all nominal WOIs within EGM signal 100.

For example, the total time duration of EGM signal 100 is 2500 ms, the accumulated nominal time durations of all WOIs (NWOI) is 80% of the total time, and therefore has a value of 2000 ms. The accumulated actual time durations of all WOIs (AWOI) within EGM signal 100 is 1984 ms. During the AWOI, a number 17 of primary peaks and a number 40 of secondary peaks remained after applying the threshold and filtering criteria described above.

In this example, processor 28 calculates the local FI using equation (1), and outputs the local FI as shown in equation (2):

$$\text{Local } FI = \frac{40}{17} \times \frac{1984}{2000} = 2.334 \quad (2)$$

In some embodiments, processor 28 is configured to output to display 26, the local FI and the calculated average AFCL, on a map of at least part of heart 23. Note that the local FI is indicative of an average number of the fragmentation peaks per AFCL between two annotated activation signals, shown in FIG. 2 as primary peaks 101, 111 and 121. Note that some sections of EGM signal 100 may comprise signals within the noise threshold, e.g., the section between WOIs 104 of primary peaks 101 and 121, which has electro-potential values between lines 103 and 105. In some embodiments, processor 28 may exclude such sections from the calculation of AFCLs and local FI, using any suitable criteria and/or predefined or learned parameters.

In other embodiments, processor 28 is configured to exclude the WOI and to identify the candidate set of secondary peaks along the entire AFCL between adjacent primary peaks. In such embodiments, the calculated local FI may comprise only the total number of identified secondary peaks, divided by the total number of primary peaks.

Figure 3:
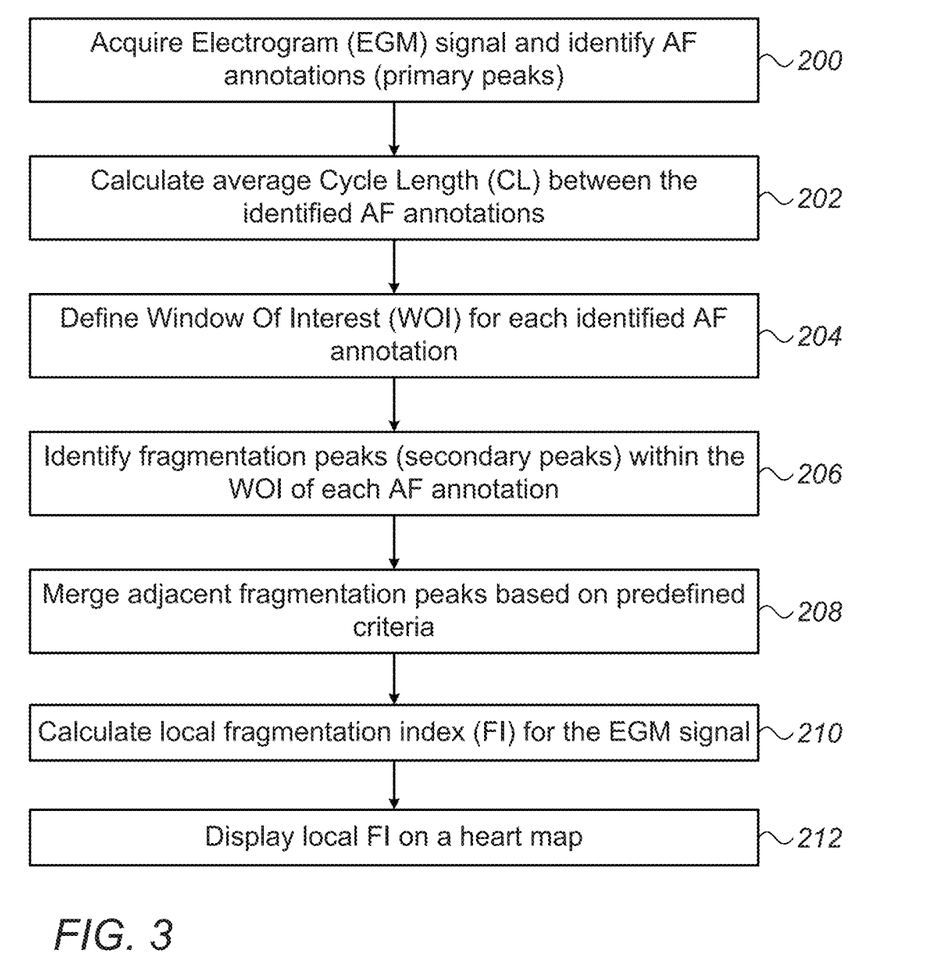
FIG. 3 is a flow chart that schematically illustrates a method for mapping atrial fibrillation (AF) in a patient heart, in accordance with an embodiment of the present invention.

A Method for Mapping Atrial Fibrillation by Calculating Local Fragmentation Index FIG. 3 is a flow chart that schematically illustrates a method for mapping AF in heart 23, in accordance with an embodiment of the present invention. The method begins at an EGM signal acquisition step 200, with acquiring EGM signal 100 using distal end 31 having one or more electrodes positioned at the given position in tissue of heart 23. In some embodiments, processor 28 receives EGM signal 100 that exhibits the AF, and identifies within EGM signal 100, the annotated activation signals, such as primary peaks 101, 111 and 121.

At a cycle length calculation step 202, processor 28 calculates the AFCL between any pair of adjacent primary peaks. In some embodiments, processor 28 calculates an average AFCL of the calculated AFCLs.

At a WOI definition step 204, processor 28 defines a WOI, such as WOI 104, having a length that is typically a fraction of the calculated AFCL, e.g., 70% or 80% of the AFCL length. In some embodiments, processor 28 calculates the WOI based on the aforementioned average AFCL length. In other embodiments, processor 28 calculates a WOI for each section of EGM signal 100, using a predefined fraction of the AFCL length of the respective section. Additionally or alternatively, processor 28 may calculate an average length of two adjacent AFCLs for the definition of a WOI located between the two respective AFCLs, or using any other suitable method for defining the WOI.

At a fragmentation peaks identification step 206, processor 28 identifies a set of candidate fragmentation peaks, such as peaks 106, 106A, 106B, 106C, 107, 108A and 108B shown in FIG. 2 above. In some embodiments, processor 28 may filter out at least some of the candidate fragmentation peaks, such as peak 107 which is within the noise threshold located between noise-threshold lines 103 and 105 shown in FIG. 2 above.

At a fragmentation peaks merging step 208, processor identifies a group of peaks comprising two or more secondary peaks that are within a predefined time interval (e.g., 20 ms) from one another and having the same sign (positive or negative). For example, a group of peaks 106A and 108A, and another group of peaks 106B and 108B. In some embodiments, processor 28 may select, within the group of peaks, the peak having the largest absolute electro-potential value and removes the other peaks from the set of secondary peaks. As depicted in FIG. 2 above, peaks 108A and 108B had the largest absolute electro-potential value and therefore, respective peaks 106A and 106B have been removed.

At a local fragmentation index (FI) calculation step 210, processor calculates the local FI using equation (1), which is described in FIG. 2 above. Processor 28 applies to equation (1), the total number of primary and secondary peaks identified and verified after the filtering and merging processes described in steps 206 and 208 above, and the total actual and nominal WOI time durations used for identifying the primary and secondary peaks. In some embodiments, the calculated local FI is indicative of the average number of secondary peaks per AFCL time duration. In the example shown in equation (2) above, the calculated value of the local FI equals 2.334, which is indicative of the average number of secondary peaks per average AFCL time duration.

In other embodiments, processor 28 may apply any other suitable equation for calculating the local FI. For example, using a median value of all the AFCLs calculated within EGM signal 100.

At a map displaying step 212, processor is configured to output, to display 26, the visualized map of at least part of heart 23, which comprises at least the given point used for acquiring EGM signal 100 and the calculated FI and one or more AFCLs.

Figure 5:
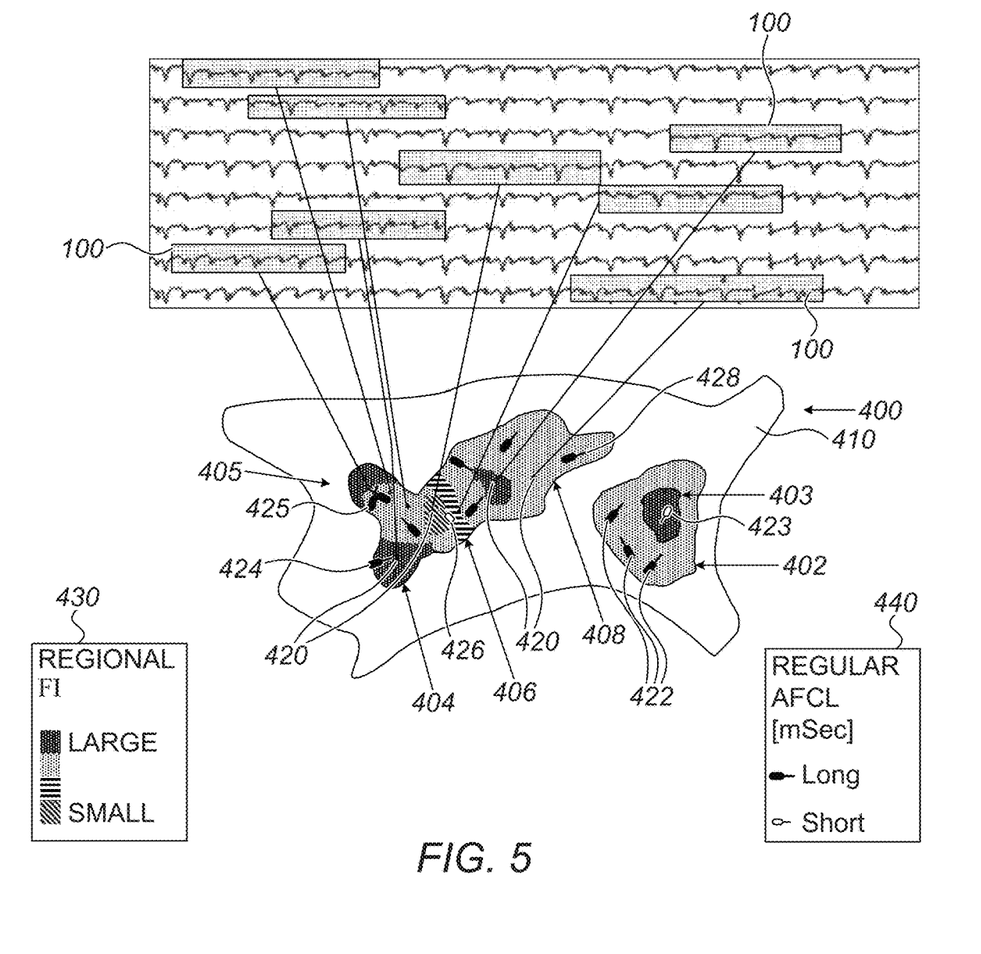
FIG. 5 is a schematic pictorial illustration of a map of a region of a patient heart, in accordance with an embodiment of the present invention.

In some embodiments, display 26 displays the local FI on the map of heart 23 received from processor 28. In some embodiments, display 26 is configured to display a visualization of the local FI using color coding or any other suitable visualization technique. For example, processor 28 and/or display 26 may assign warm colors, e.g., red, to small values of FI, and cold colors, e.g., blue, to large values of FI. As described in FIG. 2 above, display 26 may also display the one or more AFCLs overlaid on the heart map and on the displayed local FI. An exemplary embodiment of the map is shown in FIG. 5 below.

Calculating and Visualizing Regional Fragmentation Index

Figure 4:
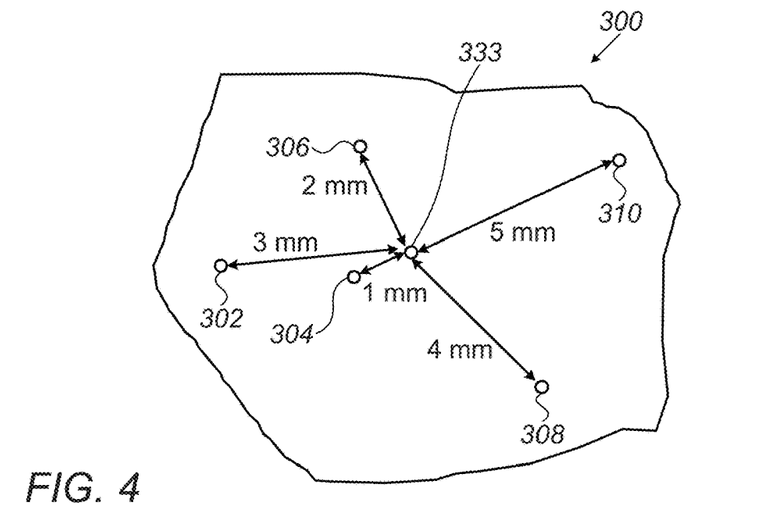
FIG. 4 is a schematic, pictorial illustration of a regional map of heart having a regional fragmentation index (FI) calculated based on multiple local FIs, in accordance with an embodiment of the present invention.

FIG. 4 is a schematic, pictorial illustration of a region 300 of heart 23 for which a regional fragmentation index (FI) is calculated based on multiple local FIs, in accordance with an embodiment of the present invention. In some embodiments, region 300 comprises points 302, 304, 306, 308 and 310, located at respective distances of 3 mm, 1 mm, 2 mm, 4 mm, and 5 mm, from a geometrical center-of-gravity (COG), referred to as COG 333 of region 300.

In some embodiments, distal end 31 of catheter 29 acquired one or more EGM signals from each of points 302, 304, 306, 308 and 310 and processor 28 calculates, e.g., using the techniques disclosed at FIGS. 2 and 3 above, a local FI for each of the points of region 300. In the example of FIG. 4, the values calculated for the local FIs of points 302, 304, 306 and 308 are 10, 5, 7 and 10, respectively.

In some embodiments, processor 28 is configured to calculate the regional FI of region 300 by calculating a weighted average over the local FIs of points 302, 304, 306, 308 and 310, using the respective distances from COG 333 for deriving the averaging weights. For a given point, the respective local FI is weighted by a weight value that is proportional to the inverse value of the distance between the given point and COG 333. For example, point 304, which is located 1 mm from COG 333, has larger weight (e.g., 1) relative to that of point 310 located 5 mm from COG 333, and therefore having a 5× smaller weight (e.g., ⅕).

In some embodiments, processor 28 calculates the weighted average by calculating a weighted sum and normalizing the weighted sum by the sum of weights. Based on the exemplary values provided above, the weights of points 302, 304, 306, 308 and 310 are 0.33, 1, 0.5, 0.25 and 0.2, respectively, and the normalization factor is the sum of weights 2.283.

In some embodiments, processor 28 calculates normalized weights for points 302, 304, 306, 308 and 310 and outputs the respective values of 0.146, 0.438, 0.219, 0.109 and 0.087, and then multiplies, for each point, the respective local FI by the respective normalized weight, and sums.

Based on the exemplary values described above, processor 28 multiplies, for each point, the local FI of points 302, 304, 306, 308 and 310 by the respective normalized weight, and outputs the respective values of weighted local FIs, 1.46, 2.19, 1.53, 1.09 and 0.35.

In some embodiments, after calculating a sum of the weighted local FIs, processor 28 outputs the regional FI having a value of 6.628. Subsequently, processor 28 outputs the calculated regional FI and the calculated AFCLs of region 300, to display 26.

Visualizing Regional Fragmentation Index and Cycle Length on Heart Map

FIG. 5 is a schematic pictorial illustration of a map 400 of a region 410 of heart 23, in accordance with an embodiment of the present invention. In some embodiments, map 400 comprises locations 420 identified by processor 28 and displayed by display 26 as locations having regular AF activity.

In some embodiments, processor 28 analyzes multiple EGM signals 100 acquired, e.g., by distal end 31, at respective locations 420 of region 410. As described in FIGS. 2 and 3 above, processor 28 identifies the primary peaks, calculates CLs and identifies, within the CLs, the AFCLs having a CL duration between 120 ms and 250 ms. As further described in FIGS. 2 and 3 above, processor 28 defines the WOIs, and identifies the fragmentation peaks within the respective WOIs. Based on the identified and verified fragmentation peaks (after filtering out the candidate fragmentation peaks not meeting the predefined threshold and/or criteria), processor 28 calculated local FI for each location 420, as described in FIGS. 2 and 3 above.

Subsequently, processor 28 calculates for each section of region 410, a regional FI, using the technique described in FIG. 4 above, and outputs to display 26, a visual map comprising the calculated AFCLs and/or one or more regional FIs. In some embodiments, display 26 is configured to display the output map using any suitable type of display, such as a gradient map using color coding.

In the example of FIG. 5, map 400 of region 410, which is displayed on display 26, comprises multiple sections having respective contours 402, 403, 404, 405, 406 and 408, each of which having a calculated regional FI. In some embodiments, map 400 comprises a legend 430, which provides any suitable type of coding of the visualized regional FI values. For example, contours 403, 404 and 405 have a "large" value of regional FI, contours 402 and 408 have a medium value of regional FI, and contour 406 has a "small" value of regional FI. In the present example, the term "large value of regional FI" refers to typical values between 3 and 7, and the term "small value of regional FI" refers to a typical value smaller than 7.

In some embodiments, map 400 further comprises AFCL markers 422, 423, 424, 425, 426 and 428, which are calculated by processor 28 (e.g., using the technique described in FIG. 2 above) in the sections represented by respective contours 402, 403, 404, 405, 406 and 408. In an embodiment, map 400 comprises a legend 440 that provides another set of coding of the visualized values of the average AFCL markers. In this example embodiment, 120 ms represents "short" AFCL values and 250 ms represents "long" AFCL values.

In some embodiments, the local FI is indicative of the average number of fragmentation peaks (also referred to herein as secondary peaks) per regular AFCL. Moreover, a short regular AFCL is indicative of a short time duration between two annotated activation signals (also referred to herein as primary peaks). In some cases, a combination of a large value of a regional FI and one or more short regular AFCLs, as shown for example in contour 403 and AFCL marker 423, respectively, may be indicative of a section having high AF activity in region 410.

In some embodiments, processor 28 may highlight on display 26 outstanding combinations, e.g., of high regional FI and short regular AFCLs, so as to draw the attention of physician 27 during the EP procedure shown for example in FIG. 1 above. In such embodiments, processor 28 may hold any set of thresholds for the regional FI and regular AFCLs, and for any combination thereof, so as to alert of any outstanding AF activities identified at specific sections or regions of heart 23.

In alternative embodiments, processor 28 may add any other suitable types of markers to be visualized on map 400, or may reduce at least one of the AFCLs or regional FIs shown on map 400 of FIG. 5.

This particular configuration of map 400 is shown by way of example, in order to illustrate certain problems that are addressed by embodiments of the present invention and to demonstrate the application of these embodiments in enhancing the performance of a system for analyzing arrhythmia, such as system 21. Embodiments of the present invention, however, are by no means limited to this specific sort of example mapping and visualizing configuration, and the principles described herein may similarly be applied to other sorts of visualizations of any medical systems.

Although the embodiments described herein mainly address arrhythmia and particularly atrial fibrillation, the methods and systems described herein can also be used in other applications, such as in persistent atrial fibrillation or in any other type arrhythmia in a human heart.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for mapping atrial fibrillation (AF) in a heart, the method comprising:
   receiving an electrogram (EGM) signal exhibiting the AF, acquired at a given position in the heart;
   identifying, in the EGM signal, two or more primary peaks and calculating a cycle length (CL) between adjacent primary peaks;
   identifying, in the EGM signal, one or more secondary peaks within the CL;
   calculating a local fragmentation index (FI) that is indicative of a number of the secondary peaks per CL; and
   visualizing the local FI on a map of at least part of the heart.

2. The method according to claim 1, wherein the heart has a region that comprises (i) the given position located at a given distance from a predefined location of the region, and (ii) at least an additional position having an additional FI and located at an additional distance from the predefined location, and comprising calculating and visualizing, based on the given distance and the additional distance, and based on the local FI and the additional FI, a regional FI of the region.

3. The method according to claim 2, wherein the predefined location comprises a geometrical center of gravity (COG) of the region, and wherein calculating and visualizing the regional FI comprises calculating, based on the given distance and the additional distance, a weighted average of at least the local FI and the additional FI.

4. The method according to claim 1, wherein identifying the one or more secondary peaks comprises merging, based on a predefined threshold, two or more adjacent secondary peaks.

5. The method according to claim 1, and comprising defining a window of interest (WOI) within the CL, and identifying the one or more secondary peaks within the WOI.

6. The method according to claim 1, wherein the EGM signal comprises multiple CLs, and wherein calculating the local FI comprises calculating, based on the multiple CLs, an average CL, and calculating an average number of the secondary peaks per the average CL.

7. A system for mapping atrial fibrillation (AF) in a heart, the system comprising:
   a processor, which is configured to: (a) receive an electrogram (EGM) signal exhibiting the AF, acquired at a given position in the heart, (b) identify, in the EGM signal, two or more primary peaks and calculate a cycle length (CL) between adjacent primary peaks, (c) identify, in the EGM signals, one or more secondary peaks within a duration of the CL, and (d) calculate a local fragmentation index (FI) that is indicative of a number of the secondary peaks per CL; and
   a display, which is configured to display the local FI on a map of at least part of the heart.

8. The system according to claim 7, wherein the heart has a region that comprises (i) the given position located at a given distance from a predefined location of the region, and (ii) at least an additional position having an additional FI and located at an additional distance from the predefined location, and wherein the processor is configured to calculate and visualize, based on the given distance and the additional distance, and based on the local FI and the additional FI, a regional FI of the region.

9. The system according to claim 8, wherein the predefined location comprises a geometrical center of gravity (COG) of the region, and wherein the processor is configured to calculate and visualize the regional FI by calculating, based on the given distance and the additional distance, a weighted average of at least the local FI and the additional FI.

10. The system according to claim 7, wherein the processor is configured to merge, based on a predefined threshold, two or more adjacent secondary peaks.

11. The system according to claim 7, wherein the processor is configured to define a window of interest (WOI) within a duration of the CL, and to identify the one or more secondary peaks within the WOI.

12. The system according to claim 7, wherein the EGM signal comprises multiple CLs, and wherein the processor is configured to calculate, based on the multiple CLs, an average CL, and to calculate an average number of the secondary peaks per the average CL.

\* \* \* \* \*